(12) United States Patent
Potuluri et al.

(10) Patent No.: US 8,417,540 B2
(45) Date of Patent: *Apr. 9, 2013

(54) SPECTRAL SIGNATURE EXTRACTION FOR DRUG VERIFICATION AND IDENTIFICATION

(75) Inventors: Prasant Potuluri, Raleigh, NC (US); Ya Xue, Niskayuna, NY (US); Yuting Qi, Cary, NC (US)

(73) Assignee: Optopo Inc., Morrisville, NC (US)

( * ) Notice: Subject to any disclaimer, the term of this patent is extended or adjusted under 35 U.S.C. 154(b) by 438 days.

This patent is subject to a terminal disclaimer.

(21) Appl. No.: 12/545,368

(22) Filed: Aug. 21, 2009

(65) Prior Publication Data
US 2010/0045978 A1 Feb. 25, 2010

Related U.S. Application Data

(63) Continuation-in-part of application No. 11/609,443, filed on Dec. 12, 2006, now Pat. No. 7,720,694, which is a continuation-in-part of application No. 11/454,923, filed on Jun. 19, 2006, now Pat. No. 7,218,395, which is a continuation-in-part of application No. 11/334,546, filed on Jan. 19, 2006, now Pat. No. 7,301,625.

(60) Provisional application No. 61/091,722, filed on Aug. 25, 2008, provisional application No. 60/725,311, filed on Oct. 12, 2005, provisional application No. 60/811,101, filed on Jun. 6, 2006, provisional application No. 60/644,522, filed on Jan. 19, 2005, provisional application No. 60/705,173, filed on Aug. 4, 2005.

(51) Int. Cl.
*G06Q 10/00* (2012.01)
*G01J 3/42* (2006.01)

(52) U.S. Cl. .......................................... 705/2; 356/326
(58) Field of Classification Search .................. 705/2
See application file for complete search history.

(56) References Cited

U.S. PATENT DOCUMENTS

| | | | |
|---|---|---|---|
| 5,850,623 A | 12/1998 | Carman, Jr. et al. | |
| 6,771,369 B2 * | 8/2004 | Rzasa et al. | 356/326 |
| 2007/0008523 A1 | 1/2007 | Kaye et al. | |
| 2007/0059356 A1 * | 3/2007 | Almarsson et al. | 424/464 |
| 2008/0059240 A1 | 3/2008 | Potuluri et al. | |
| 2008/0137080 A1 * | 6/2008 | Bodzin et al. | 356/300 |

* cited by examiner

*Primary Examiner* — Hiep V Nguyen
(74) *Attorney, Agent, or Firm* — John R. Kahsa; Kasha Law LLC

(57) ABSTRACT

Systems and methods perform signature extraction from an acquired spectrum of a pharmaceutical. An acquired spectrum of the pharmaceutical is measured using a spectrometer. The acquired spectrum is obtained from the spectrometer using a processor. A system-response function of the spectrometer is removed from the acquired spectrum using the processor. An intensity of the acquired spectrum is normalized to a predetermined scale using the processor. Fluorescence is removed from the acquired spectrum using the processor. Finally, an extracted signature of the pharmaceutical is obtained from the remainder of the acquired spectrum using the processor. If the acquired spectrum of the pharmaceutical is measured by the spectrometer through a container holding the pharmaceutical, a spectrum of the container is removed from the remainder of the acquired spectrum to produce the extracted signature of the pharmaceutical using the processor.

30 Claims, 7 Drawing Sheets

SPECTRAL SIGNATURE EXTRACTION FOR DRUG VERIFICATION AND IDENTIFICATION

CROSS-REFERENCE TO RELATED APPLICATION

This application is a continuation-in-part application of U.S. patent application Ser. No. 11/609,443, filed Dec. 12, 2006 now U.S. Pat. No. 7,720,694 (the "'443 application"). This application also claims the benefit of U.S. Provisional Patent Application No. 61/091,722, filed Aug. 25, 2008. The '443 application is a continuation-in-part application of U.S. patent application Ser. No. 11/454,923 (the "'923 application"), filed Jun. 19, 2006 now U.S. Pat. No. 7,218,395 (the "'395 patent"). The '923 application is a continuation-in-part application of U.S. patent application Ser. No. 11/334,546 (the "'546 application"), filed Jan. 19, 2006 now U.S. Pat. No. 7,301,625 (the "'625 patent). The '923 application also claims the benefit of U.S. Provisional Patent Application No. 60/725,311, filed Oct. 12, 2005, and U.S. Provisional Patent Application No. 60/811,101, filed Jun. 6, 2006. The '546 application claims the benefit of U.S. Provisional Patent Application No. 60/644,522, filed Jan. 19, 2005, and U.S. Provisional Patent Application No. 60/705,173, filed Aug. 4, 2005. All of the above mentioned applications are incorporated by reference herein in their entireties.

BACKGROUND OF THE INVENTION

1. Field of the Invention

Embodiments of the present invention relate generally to systems and methods of signature extraction applied to the identification and verification of pharmaceuticals. More specifically, embodiments of the present invention relate to an intelligent computational system that extracts signatures from the spectra of pharmaceuticals contained in a vial using methods of signal processing and spectral analysis.

2. Background Information

In recent years, pharmacists' dispensing accuracy has become a rising issue throughout the country, especially in high-volume pharmacy settings (e.g., retail and hospitals). A dispensing error occurs when a patient is dispensed a medicine other than what is prescribed to him. A dispensing error could injure or kill a patient. Reducing the dispensing error rate is a critical factor in pharmacy risk management. It is desirable to have an instrument that can automatically validate dispensed pharmaceuticals with high accuracy and efficiency.

U.S. Pat. No. 7,218,395 (the "395 patent") to Stephen T. Kaye et al., which is incorporated herein by reference in its entirety, describes a rapid pharmaceutical identification system. A Raman spectrometer measures the spectrum of a pharmaceutical in a vial, with no need of opening the vial cap. The collected spectrum is matched against a database that contains a plurality of spectral signatures corresponding to known pharmaceuticals. Based on the matching results, the system validates whether the vial contains the pharmaceutical consistent with the prescription (i.e., a scanned barcode).

The 395 patent has a detailed description of a sensor and system framework, and a brief description of the algorithmic methods of matching the collected spectrum to the spectral signature database. For example, the 395 patent lists several algorithms used to achieve this match including a correlation search and a first derivative search. The 395 patent also explains that the sensor identifies the tablets with the spectra in database that correlates with the best match.

In view of the foregoing, it can be appreciated that a substantial need exists for additional systems and methods that can advantageously match the collected spectrum to the spectral signature database of a pharmaceutical identification and verification system.

BRIEF SUMMARY OF THE INVENTION

In various embodiments, systems and methods are used to acquire a spectrum and extract a signature of a pharmaceutical from the acquired spectrum, with the challenges above addressed. These systems and methods integrate a set of algorithms related to signal processing and spectral analysis. One method includes five software modules: a spectrum acquisition module, a system-response correction module, an exposure-time normalization module, a baseline correction module, and an extraction collection module.

A spectrum acquired by a spectrometer is obtained by the spectrum acquisition module and sent to the system-response correction module. Every instrument has its own system-response function and the output signal (i.e., the acquired spectrum) is a convolution of an input signal (i.e., the actual spectrum) and the system-response function. The system-response function can be characterized by a Raman spectrum obtained from a National Institute of Standards and Technology (NIST) standard glass material. The objective of the system-response correction module is to recover the actual spectrum by reversing the effects of convolution.

The exposure-time normalization module is used to normalize an intensity of the acquired spectrum to a predetermined scale. To optimize measurement performance, pharmaceuticals are exposed to the laser (transmitted by the spectrometer) for a variable time length ranging from 50 ms to 20 s, for example. It is known that the intensity of the acquired spectrum is linearly proportional to the exposure time. The variations due to the exposure times have to be normalized to a certain standard, in order to quantify the spectrum strength of a pharmaceutical.

The baseline correction module is used remove fluorescence from the spectrum. Generally, a Raman spectrum has a few sharp peaks and a flat baseline, while a fluorescence spectrum is relatively smooth with a sloped or curved baseline. Based on these observations, methods have been designed to separate a Raman spectrum and fluorescence spectrum by fitting a baseline to the mixed spectrum. The baseline corresponds to the fluorescence spectrum, and the residual of subtracting the baseline corresponds to the Raman spectrum.

Finally, the extraction collection module is used to obtain the extracted signature of the pharmaceutical from the remainder of the acquired spectrum. If, however, the acquired spectrum of the pharmaceutical is measured by the spectrometer through a container holding the pharmaceutical, the remainder of the acquired spectrum includes the spectrum of the pharmaceutical and the spectrum of the container. The latter can be measured through lab experiments. Therefore, it is important to determine the proportion of two spectra in the linear mix. Several methods can be used to extract the pharmaceutical spectrum from the mixed spectrum.

Figure 1:
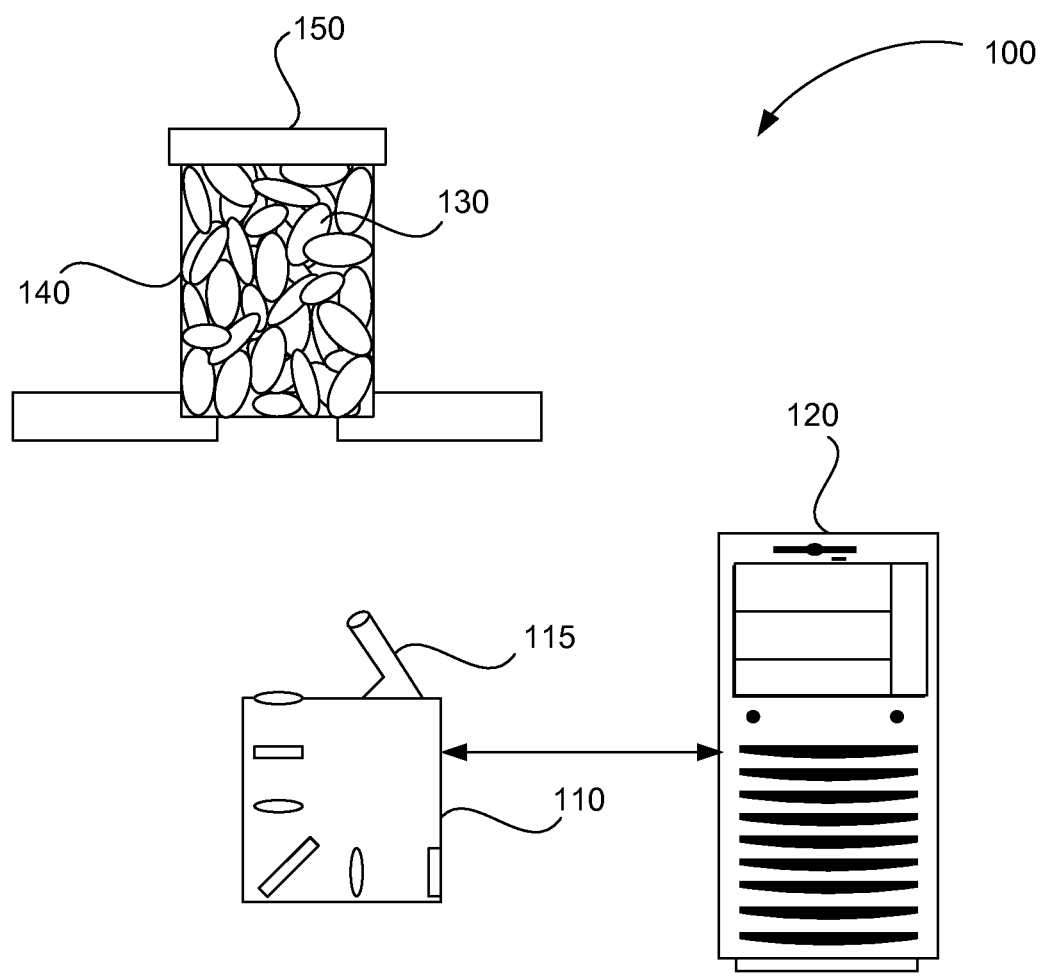
FIG. 1 is a schematic diagram of a system for signature extraction, in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

Spectral signature extraction is an important component of a pharmaceutical identification and verification system, such as the system described in the 395 patent. A system of the '395 patent uses a static multimode multiplex spectrometer (MMS). A static MMS is described in the '101 patent. A two-dimensional (2D) coded aperture static MMS is described in the '625 patent.

The spectrum acquired by a spectrometer is actually a superposition of several components. This superposition can occur for a number of reasons. For example, in Raman spectroscopy, it is sometimes the case that spectra can be contaminated by fluorescence. Also, if the spectrometer reads though a vial, it is likely that the spectrometer will receive scattering from the vial material. Therefore, in Raman spectroscopy, it is possible that the acquired spectrum is a superposition of the pharmaceutical Raman spectrum, the pharmaceutical fluorescence spectrum, the vial Raman spectrum, and the vial fluorescence spectrum. Among these spectra, only the pharmaceutical Raman spectrum is the signature that distinguishes a pharmaceutical from others. The pharmaceutical fluorescence spectrum could change, but not the Raman spectrum. As a result, in various embodiments, the pharmaceutical Raman spectrum is extracted from the acquired spectrum before applying matching algorithms. The extraction of the pharmaceutical Raman spectrum is called signature extraction.

Several factors complicate the task of signature extraction: (i) both fluorescence spectra (pharmaceutical and vial) are not measurable, (ii) the proportion of the four components changes constantly, (iii) the system response of the Raman spectrometer introduces non-linear distortions to the acquired spectrum, and (iv) there exist manufacture variances, measurement variances, and random noise that further distort the spectrum. These factors, plus requirements in efficiency, accuracy, and robustness, make the task of signature extraction challenging.

In various embodiments systems and methods perform signature extraction from the spectrum of a pharmaceutical through an open or closed vial for pharmaceutical verification and identification. A signature is the collection of features that characterize an object and its behavior. It can be directly measurable or it can be extracted from a measured signal, depending on the specific applications and signal characteristics. In various embodiments, a signature refers to the unique spectrum a pharmaceutical emits when it is exposed to a laser with a certain wavelength. A pharmaceutical or a particular strength of a pharmaceutical can be verified by matching its signature against a database that contains spectral signatures corresponding to known pharmaceuticals or strengths of pharmaceuticals. The spectrum captured by the spectrometer is actually a superposition of multiple spectra, as discussed above. Therefore, it is important to extract the signature (i.e., the pharmaceutical spectrum) before implementing the matching algorithms.

FIG. 1 is a schematic diagram of a system 100 for signature extraction, in accordance with an embodiment of the present invention. System 100 includes spectrometer 110 and processor 120. Processor 120 is in communication with spectrometer 110. This communication can include, but is not limited to, wired or wireless data communication. Spectrometer 110 includes laser 115, for example. Spectrometer 110 can include, but is not limited to, a Raman spectrometer, an MMS, a 2D coded aperture static MMS and/or a FTIR spectrometer. Processor 120 can include, but is not limited to, a computer, a microprocessor, an application specific integrated circuit, a field programmable gate array (FPGA), or any device capable of executing a series of instructions.

Spectrometer 110 of system 100 acquires a spectrum of pharmaceutical 130 and container 140 through the bottom of container 140. In various embodiments, spectrometer 110 can also acquire a spectrum of pharmaceutical 130 and container 140 through a side of container 140, or spectrometer 110 can acquire a spectrum of pharmaceutical 130 and lid 150 through the top of container 140. In various embodiments and alternatively spectrometer 110 can acquire a spectrum of pharmaceutical 130 without the spectrum of container 140 by illuminating pharmaceutical 130 through the top of container 140 without lid 150, for example.

Pharmaceutical 130 can include, but is not limited to, a medication or a controlled substance. Pharmaceutical 130 is shown in system 100 as a pharmaceutical solid. A pharmaceutical solid is, for example, a pill. A pill can include, but is not limited to, a tablet, a caplet, a suppository, a gelcap, or a capsule. In various embodiments, pharmaceutical 130 can also include a liquid or a powder, for example. Container 140 is shown as a prescription vial. In various embodiments, container 140 can also include a bottle, blister pack, Intravenous bags, syringes, cuvettes or trays, for example. Processor 120 receives the acquired spectrum from spectrometer 110. Processor 120 removes a system-response function of spectrometer 110 from the acquired spectrum. For example, processor 120 removes a system-response function of spectrometer 110 by reversing a convolution of the acquired spectrum and the system-response function of spectrometer 110.

Processor 120 normalizes an intensity of the acquired spectrum to a predetermined scale. For example, processor 120 normalizes an intensity of the acquired spectrum to a predetermined scale by dividing the intensity by an exposure time of spectrometer 110 to pharmaceutical 130 normalized to the predetermined scale.

Processor 120 removes fluorescence from the acquired spectrum. In various embodiments, the fluorescence from the acquired spectrum can include fluorescence from container 140. Processor 120 removes fluorescence from the acquired spectrum by fitting a baseline spectrum of the fluorescence to the acquired spectrum and removing the baseline spectrum from the acquired spectrum. Fitting a baseline spectrum of the fluorescence to the acquired spectrum can include, but is not limited to, applying a line algorithm, a horizontal algorithm, a peak detection algorithm, or a linear least squares regression algorithm.

Finally, processor 120 obtains an extracted signature of pharmaceutical 130 from the remainder of the acquired spectrum. If, however, spectrometer 110 measures the acquired spectrum through container 140, processor 120 additionally removes a spectrum of container 140 from the remainder of the acquired spectrum to obtain the extracted signature of pharmaceutical 130. Additionally removing a spectrum of container 140 from the remainder of the acquired spectrum to produce the extracted signature of pharmaceutical 130 can include, but is not limited to, applying an optimization algorithm, a principal component analysis algorithm, a blind source separation algorithm, a Fourier-domain analysis algorithm, or a wavelet-domain analysis algorithm. Determining a spectrum of container 140 can also include acquiring a spectrum of empty container 140, removing a system-response function of the spectrometer from the acquired spectrum, normalizing the intensity of the acquired spectrum, and obtaining the spectrum of container 140 from the remainder of the acquired spectrum.

In various embodiments, processor 120 can remove the spectrum of a known compound in pharmaceutical 130 in a fashion similar to the removal of the spectrum of container 140. For example, if pharmaceutical 130 includes a known compound, processor 120 additionally removes a spectrum of the known compound from the remainder of the acquired spectrum to obtain the extracted signature of pharmaceutical 130. Additionally removing a spectrum of the known compound from the remainder of the acquired spectrum to produce the extracted signature of pharmaceutical 130 can include, but is not limited to, applying an optimization algorithm, a principal component analysis algorithm, a blind source separation algorithm, a Fourier-domain analysis algorithm, or a wavelet-domain analysis algorithm.

Figure 2:
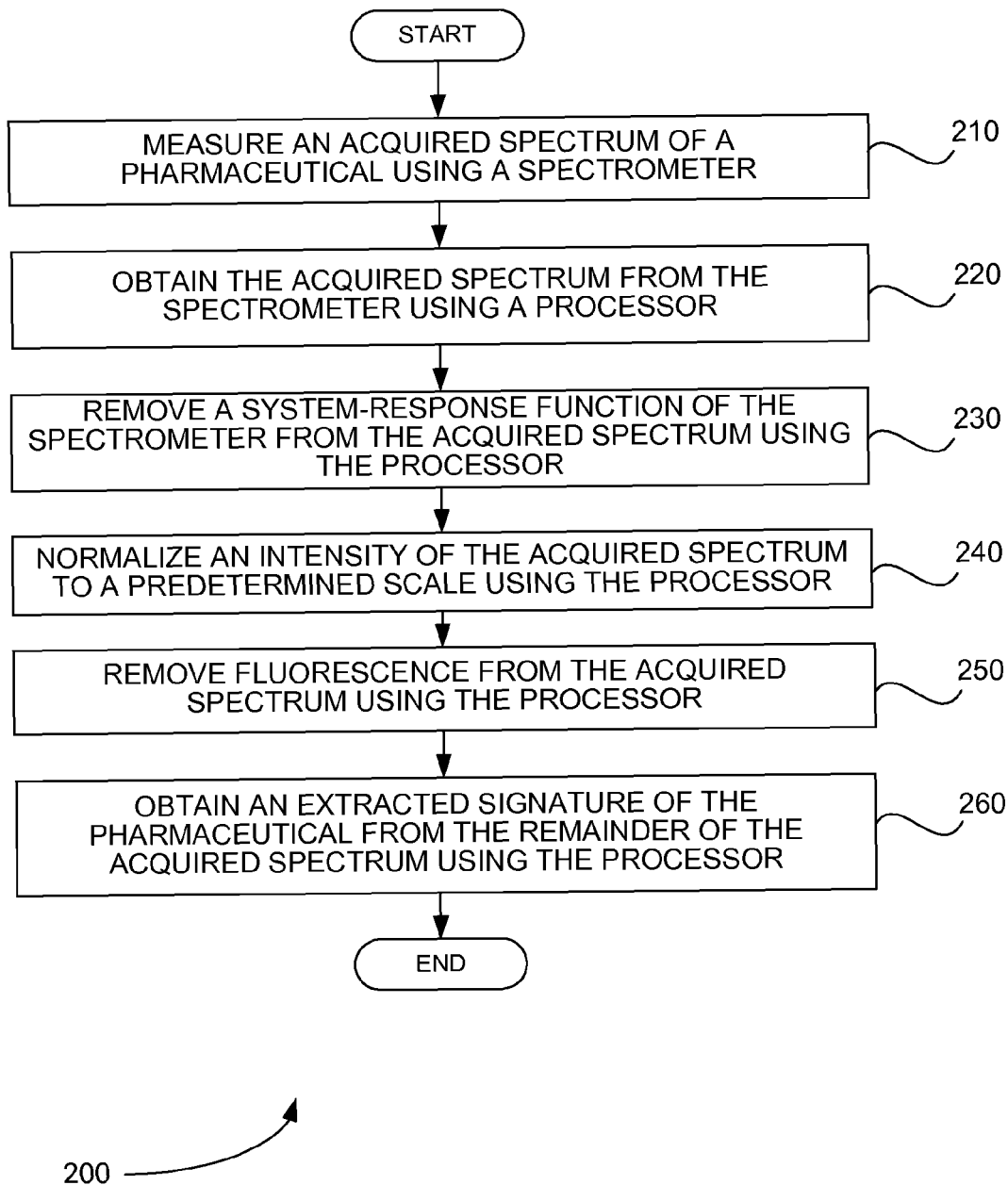
FIG. 2 is a flowchart showing a method for signature extraction, in accordance with an embodiment of the present invention.

FIG. 2 is a flowchart showing a method 200 for signature extraction, in accordance with an embodiment of the present invention.

In step 210 of method 200, an acquired spectrum of a pharmaceutical is measured using a spectrometer.

In step 220, the acquired spectrum is obtained from the spectrometer using a processor.

In step 230, a system-response function of the spectrometer is removed from the acquired spectrum using the processor.

In step 240, an intensity of the acquired spectrum is normalized to a predetermined scale using the processor.

In step 250, fluorescence is removed from the acquired spectrum using the processor.

Finally in step 260, an extracted signature of the pharmaceutical is obtained from a remainder of the acquired spectrum using the processor.

In various embodiments, if the acquired spectrum of the pharmaceutical is measured by the spectrometer through a container holding the pharmaceutical, a spectrum of the container is removed from the remainder of the acquired spectrum to produce the extracted signature of the pharmaceutical using the processor.

In various embodiments, if the pharmaceutical includes a known compound, a spectrum of the known compound is removed from the remainder of the acquired spectrum to produce the extracted signature of the pharmaceutical using the processor.

Figure 3:
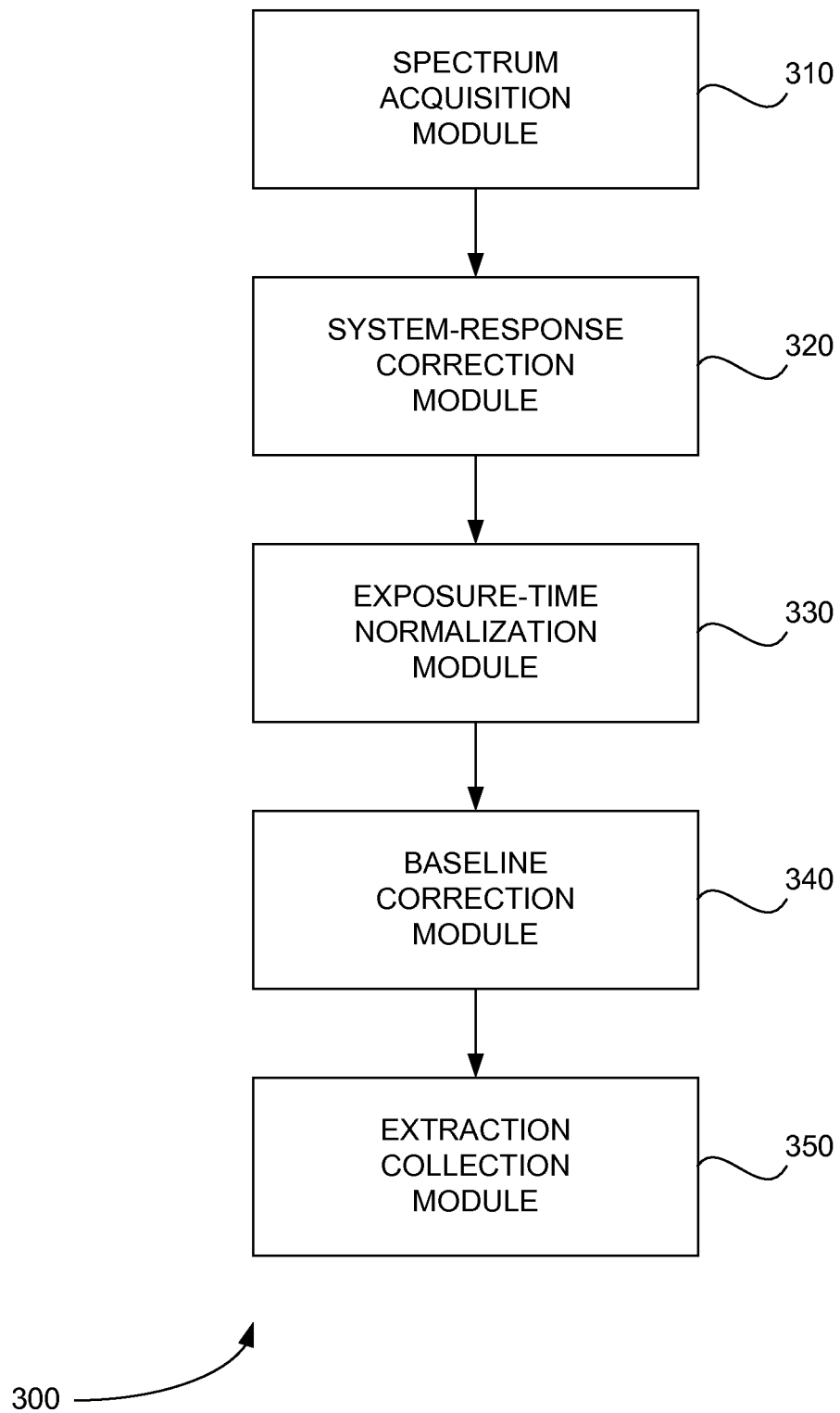
FIG. 3 is a schematic diagram of a software system for signature extraction, in accordance with an embodiment of the present invention.

FIG. 3 is a schematic diagram of a software system 300 for signature extraction, in accordance with an embodiment of the present invention. System 300 includes distinct software modules embodied on a computer-readable medium, for example. The distinct software modules include a spectrum acquisition module 310, a system-response correction module 320, an exposure-time normalization module 330, a baseline correction module 340, and an extraction collection module 350.

Spectrum acquisition module 310 is used to obtain an acquired spectrum of a pharmaceutical from a spectrometer. Spectrum acquisition module 310 can, for example, read data from the spectrometer or receive data from the spectrometer.

System-response correction module 320 is used to remove a system-response function of the spectrometer from the acquired spectrum. System-response correction module 320 can use a National Institute of Standards and Technology (NIST) standard correction method, for example. The NIST standard refers to a NIST glass reference material whose luminescence spectrum is calibrated.

Figure 4:
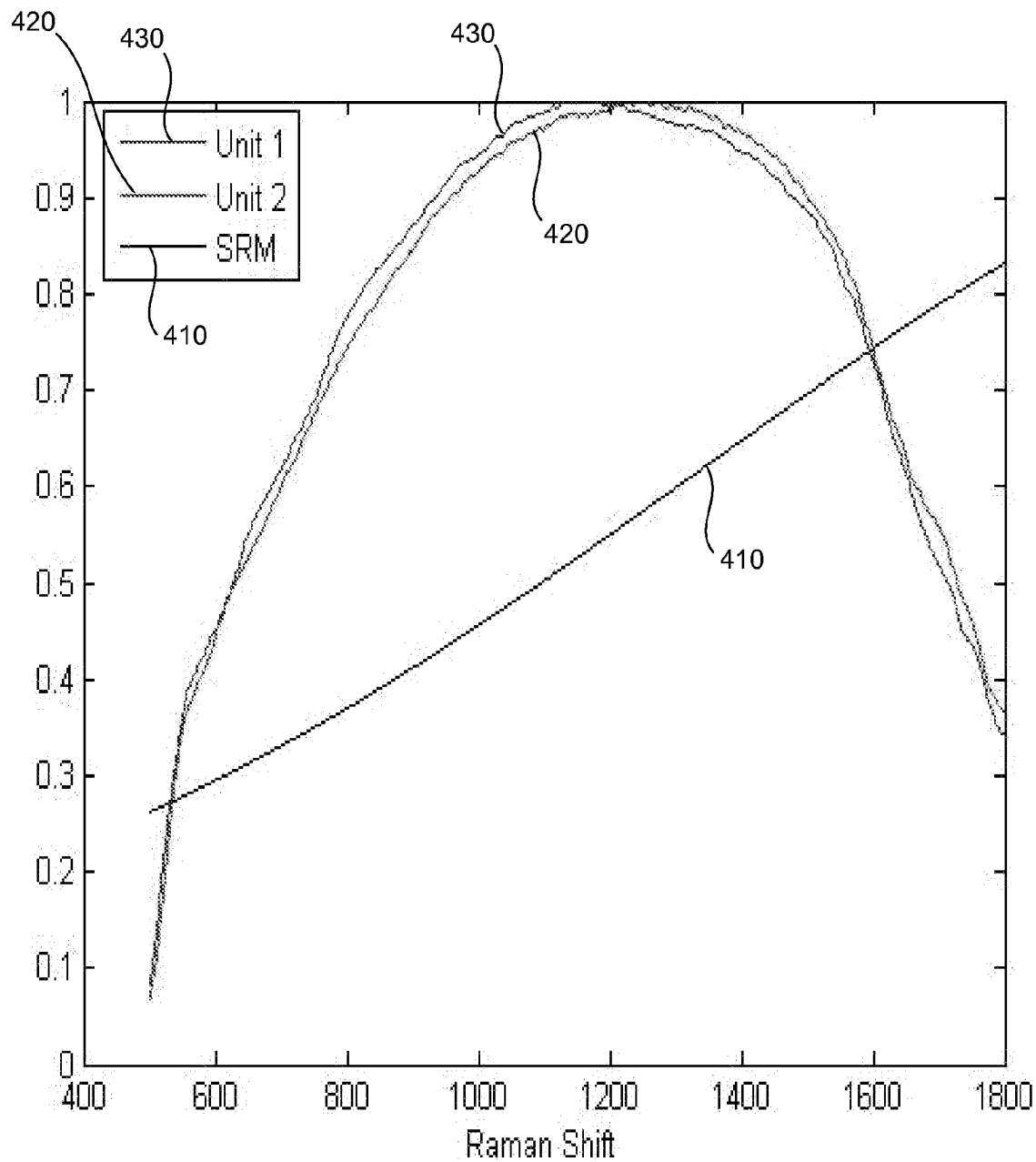
FIG. 4 is an exemplary plot showing a theoretical NIST spectrum and the actual measured spectrum of a first instrument and the actual measured spectrum of a second instrument, in accordance with an embodiment of the present invention.

FIG. 4 is an exemplary plot 400 showing a theoretical NIST spectrum 410, the actual measured spectrum 420 of a first spectrometer and the actual measured spectrum 430 of a second spectrometer, in accordance with an embodiment of the present invention. The response curve of an ideal Raman spectrometer is close to the sloped straight line of theoretical NIST spectrum 410. The actual response curve of a real instrument is a concave curve such as spectrum 420 of the first spectrometer and spectrum 430 of the second spectrometer.

Returning to FIG. 3, the ratio of the ideal response curve to the actual response curve at every wavelength is stored by system-response correction module 320 as a vector of correction coefficients, for example. The measured pharmaceutical spectrum is multiplied (element-by-element) by the vector of correction coefficients such that the distortion effect of the system-response function is reversed.

Exposure-time normalization module 330 is used to normalize an intensity of the acquired spectrum to a predetermined scale. The exposure time of the spectrometer to the pharmaceutical is a parameter that is used by exposure-time normalization module 330. It is pharmaceutical-specific. The acquired spectrum is divided by the corresponding exposure time, such that it is normalized to a predetermined scale. This scale is, for example, a one second scale.

Baseline correction module 340 is used to remove fluorescence from the acquired spectrum. Baseline correction module 340 can use, but is not limited to, techniques that include an optimization algorithm, a line algorithm, a horizontal algorithm, a peak detection algorithm, or a linear least squares regression algorithm.

In various embodiments, the problem of baseline correction is modeled as a constrained optimization problem. A constrained optimization problem involves, for example, finding a curve that doesn't exceed any point on the spectrum and has the minimal distance from the spectrum. To improve algorithm robustness to noise, the constraint condition is relaxed, as the curve can go above the spectrum to a certain distance, which corresponds to the noise level. The distance is estimated by dividing the spectrum into many small segments and taking the minimal standard derivation of the intensity over all segments.

The baseline curve could be polynomial or piece-wise polynomial with additional boundary conditions. Standard constrained optimization techniques may be used to find the coefficients of the polynomial function(s).

Extraction collection module 350 is used to obtain the extracted signature of the pharmaceutical from the remainder of the acquired spectrum. It is important to note that only the middle range of the acquired spectrum is used by extraction collection module 350 and all of the other modules of software system 300. Relatively large distortions appear at the edge of the detector of a Raman spectrometer. That leads to signification measurement errors in the acquired spectrum's head and tail parts.

If the acquired spectrum of the pharmaceutical is measured by the spectrometer through a container holding the pharmaceutical, a container subtraction module is added to software system 300. The container subtraction module is used to remove a spectrum of the container from the remainder of the acquired spectrum. Extraction collection module 350 then obtains the extracted signature of the pharmaceutical from the remainder of the acquired spectrum.

Before applying the container subtraction module, there are only two components left in the spectrum. The spectrum can be written in terms of these components as $$\vec{X} = \vec{X}_p + \alpha \vec{X}_v,$$

where $\vec{X}_p$ is the pharmaceutical Raman spectrum, $\vec{X}_v$ is the vial Raman spectrum, and $\alpha$ is a weighting factor (scalar). The vial Raman spectrum, $\vec{X}_v$, is stored in the system as a calibration parameter. Hence, the task is to recover $\vec{X}_p$ with $\alpha$ unknown, and $\vec{X}$ and $\vec{X}_v$ given.

A few methods developed in the fields of signal processing and pattern recognition can be used for vial subtraction, such as optimization, principle component analysis (PCA), blind source separation, Fourier-domain analysis, or wavelet-domain analysis.

In various embodiments, an optimization method can be used for vial subtraction, for example. An iterative optimization algorithm includes the following steps:

1. Removing noise by filtering. Any filtering techniques can be implemented.
2. Initializing optimization step size and search region.
3. Searching for an optimal value of $\alpha$ according to a certain objective function. The function may be designed for specific applications. An example is to maximize the smoothness of the residual spectrum $\vec{X} - \alpha \vec{X}_v$.
4. Determining if an accuracy threshold is met. If not, reduce step size and search region and go to 3.
5. Estimating $\vec{X}_p$ given the optimal value of $\alpha$.

Methods of vial subtraction can be leveraged to other applications. A pharmaceutical composition can include multiple compounds. For such a pharmaceutical Raman spectrum, $\vec{X}_p$ is a superposition of the spectra of the compounds. In some cases, it is necessary to subtract one of the spectra. For example, Hydrocodone-APAP and Oxycodone-APAP both contain the active substance acetaminophen (APAP), which has a very strong Raman scattering. Both pharmaceuticals' spectra are similar to that of pure APAP. A better way to separate them is to subtract the known APAP spectrum from pharmaceutical Raman spectrum and then do matching against the database. It is possible to extend the methods of vial subtraction to compound subtraction, by substituting vial spectrum with the known compound spectrum.

Figure 5:
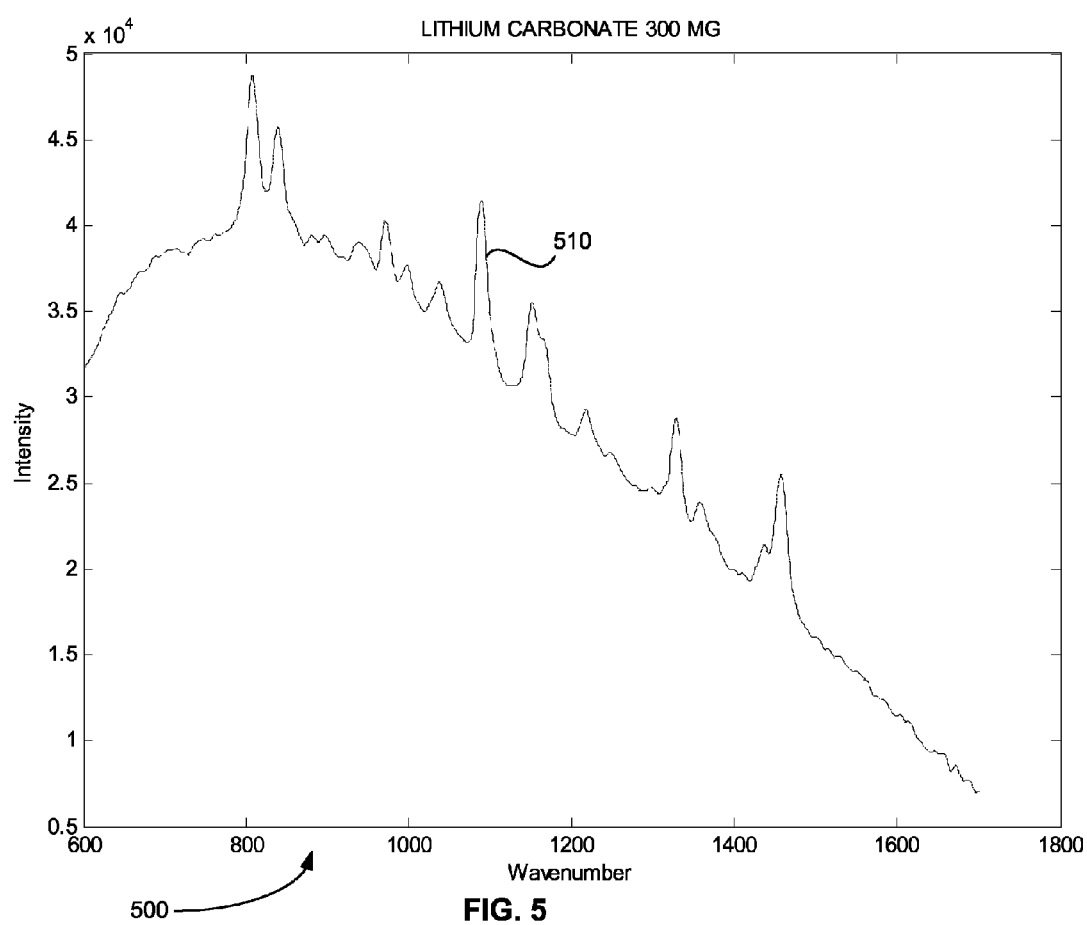
FIG. 5 is an exemplary plot showing the acquired spectrum of Lithium Carbonate 300MG, in accordance with an embodiment of the present invention.

FIG. 5 is an exemplary plot 500 showing the acquired spectrum 510 of Lithium Carbonate 300MG, in accordance with an embodiment of the present invention.

Figure 6:
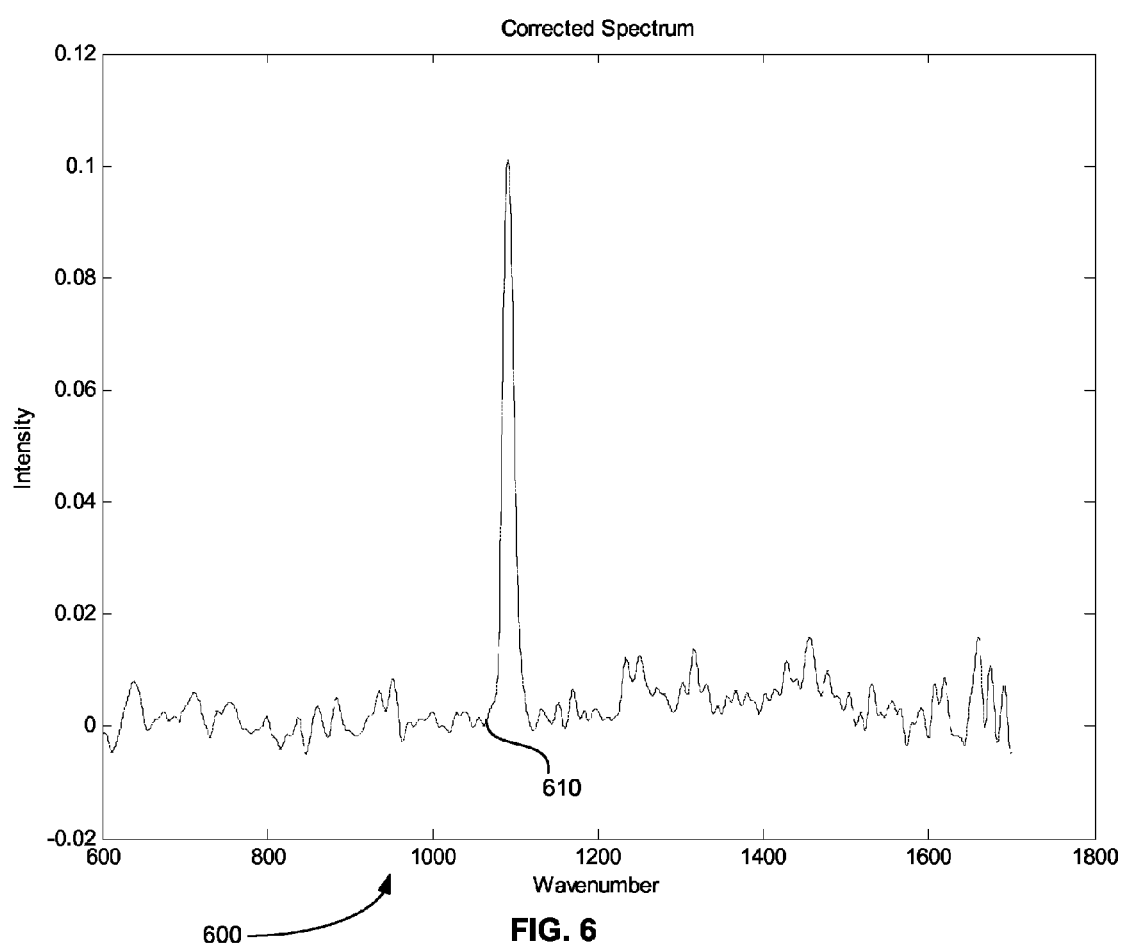
FIG. 6 is an exemplary plot showing the extracted signature of Lithium Carbonate 300MG, in accordance with an embodiment of the present invention.

FIG. 6 is an exemplary plot 600 showing the extracted signature 610 of Lithium Carbonate 300MG, in accordance with an embodiment of the present invention of the present invention.

Figure 7:
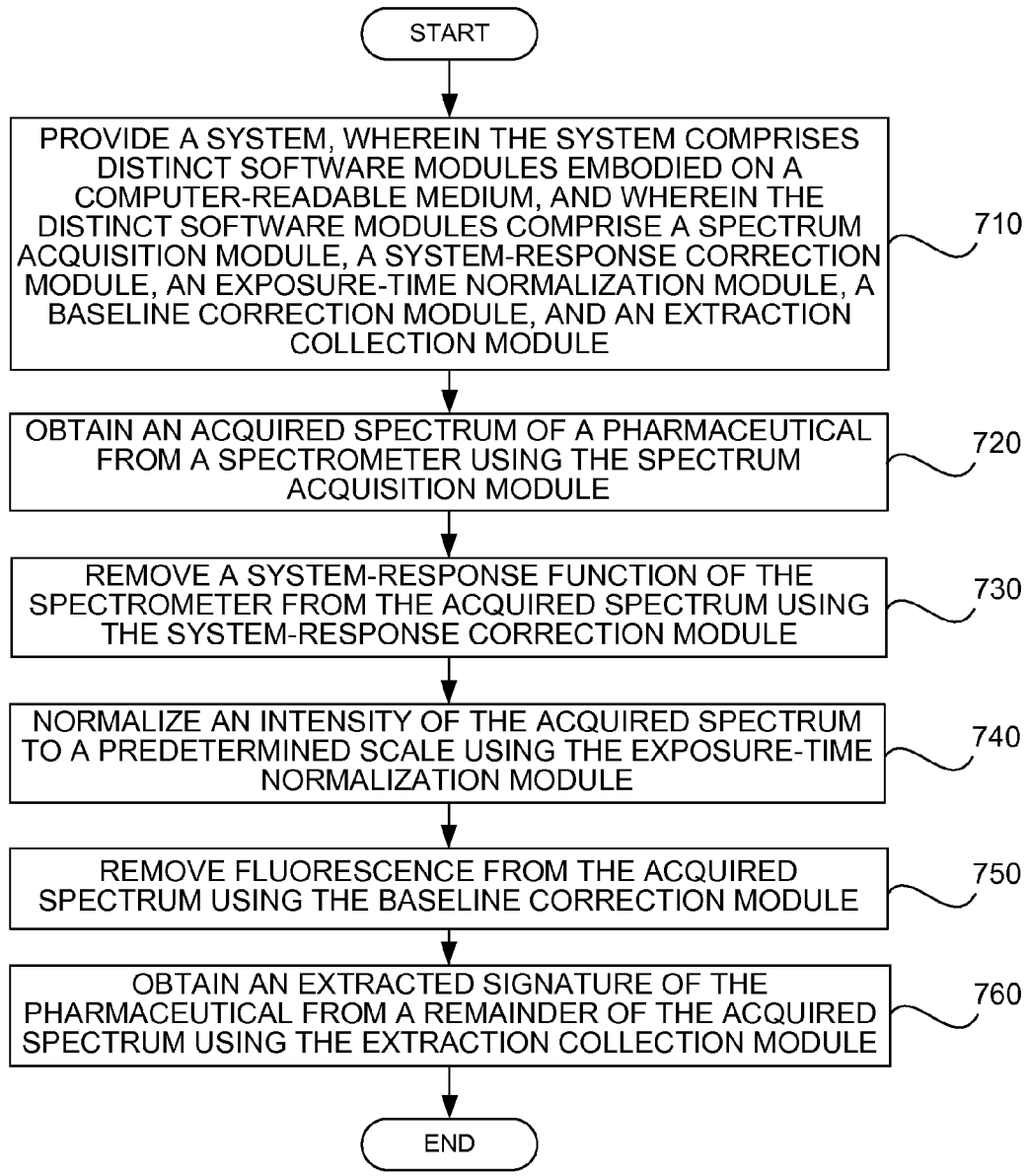
FIG. 7 is a flowchart showing a method for signature extraction using a software system, in accordance with an embodiment of the present invention.

FIG. 7 is a flowchart showing a method 700 for signature extraction using a software system, in accordance with an embodiment of the present invention.

In step 710 of method 700, a system is provided that includes distinct software modules embodied on a computer-readable medium. The distinct software modules include a spectrum acquisition module, a system-response correction module, an exposure-time normalization module, a baseline correction module, and an extraction collection module.

In step 720, an acquired spectrum of a pharmaceutical is obtained from a spectrometer using the spectrum acquisition module.

In step 730, a system-response function of the spectrometer is removed from the acquired spectrum using the system-response correction module.

In step 740, an intensity of the acquired spectrum is normalized to a predetermined scale using the exposure-time normalization module.

In step 750, fluorescence is removed from the acquired spectrum using the baseline correction module.

Finally in step 760, an extracted signature of the pharmaceutical is obtained from the remainder of the acquired spectrum using the extraction collection module.

As described above, if the acquired spectrum of the pharmaceutical is measured by the spectrometer through a container holding the pharmaceutical, a container subtraction module is added the system. The container subtraction module is used to remove a spectrum of the container from the remainder of the acquired spectrum. The extraction collection module then obtains the extracted signature of the pharmaceutical from the remainder of the acquired spectrum.

Also as described above, if the pharmaceutical includes a known compound, a compound subtraction module is added the system. The compound subtraction module is used to remove a spectrum of the known compound from the remainder of the acquired spectrum. The extraction collection module then obtains the extracted signature of the pharmaceutical from the remainder of the acquired spectrum.

In accordance with an embodiment of the present invention, instructions or program code adapted to be executed by a processor to perform a method are stored on a computer-readable medium. The computer-readable medium can be a device that stores digital information. For example, a computer-readable medium includes a read-only memory (e.g., a Compact Disc-ROM ("CD-ROM") as is known in the art for storing software. The computer-readable medium can be accessed by a processor suitable for executing instructions or program code adapted to be executed. The terms "instructions configured to be executed," "program code adapted to be executed," and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

In the foregoing detailed description, systems and methods in accordance with embodiments of the present invention have been described with reference to specific exemplary embodiments. Accordingly, the present specification and figures are to be regarded as illustrative rather than restrictive.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

We claim:

1. A system for signature extraction, comprising:
a spectrometer that measures an acquired spectrum of a pharmaceutical through the bottom, side, or top of a closed container; and
a processor in communication with the spectrometer that stores a calibration spectrum of the closed container;
receives the acquired spectrum from the spectrometer,
removes a system-response function of the spectrometer from the acquired spectrum,
normalizes an intensity of the acquired spectrum to a predetermined scale by dividing the intensity by an exposure time of the spectrometer to the pharmaceutical,
removes fluorescence from the acquired spectrum, and
subtracts the stored calibration spectrum of the closed container from a remainder of the acquired spectrum to obtain an extracted signature of the pharmaceutical.

2. The system of claim 1, wherein the processor subtracts the stored calibration spectrum of the closed container from a remainder of the acquired spectrum to obtain an extracted signature of the pharmaceutical by solving equation:

$$\vec{X} = \vec{X}_P + \alpha \vec{X}_V,$$

where $\vec{X}$ is the remainder of the acquired spectrum, $\vec{X}_p$ is the extracted signature of the pharmaceutical, $\vec{X}_v$ is the stored calibration spectrum of the closed container, and $\alpha$ is a weighting factor (scalar).

3. The system of claim 2, wherein the processor solves the equation, $\vec{X} = \vec{X}_P + \alpha \vec{X}_V$, for $\vec{X}_p$, the extracted signature of the pharmaceutical, and $\alpha$, the weighting factor using one of an optimization algorithm, a principal component analysis algorithm, a blind source separation algorithm, a Fourier-domain analysis algorithm, or a wavelet-domain analysis algorithm.

4. The system of claim 1, wherein if the pharmaceutical comprises a known compound, the processor additionally removes a spectrum of the known compound from the remainder of the acquired spectrum to obtain a second extracted signature of the pharmaceutical.

5. The system of claim 4, wherein the processor additionally removes a spectrum of the known compound from the remainder of the acquired spectrum to produce the second extracted signature of the pharmaceutical using one of an optimization algorithm, a principal component analysis algorithm, a blind source separation algorithm, a Fourier-domain analysis algorithm, or a wavelet-domain analysis algorithm.

6. The system of claim 1, wherein the spectrometer comprises a Raman spectrometer.

7. The system of claim 1, wherein the spectrometer comprises a multimode multiplex spectrometer.

8. The system of claim 1, wherein the processor removes a system-response function of the spectrometer by reversing a convolution of the acquired spectrum and the system-response function of the spectrometer.

9. The system of claim 1, wherein the processor removes fluorescence from the acquired spectrum by fitting a baseline spectrum of the fluorescence to the acquired spectrum and removing the baseline spectrum from the acquired spectrum.

10. The system of claim 1, wherein fitting a baseline spectrum of the fluorescence comprises a line algorithm.

11. The system of claim 1, wherein fitting a baseline spectrum of the fluorescence comprises a horizontal algorithm.

12. The system of claim 1, wherein fitting a baseline spectrum of the fluorescence comprises a peak detection algorithm.

13. The system of claim 1, wherein fitting a baseline spectrum of the fluorescence comprises a linear least squares regression algorithm.

14. A method for signature extraction, comprising:
measuring an acquired spectrum of a pharmaceutical through the bottom, side, or top of a closed container using a spectrometer;
storing a calibration spectrum of the closed container using a processor;
obtaining the acquired spectrum from the spectrometer using the processor;
removing a system-response function of the spectrometer from the acquired spectrum using the processor;
normalizing an intensity of the acquired spectrum to a predetermined scale using the processor by dividing the intensity by an exposure time of the spectrometer to the pharmaceutical;
removing fluorescence from the acquired spectrum using the processor; and
subtracting the stored calibration spectrum of the closed container from a remainder of the acquired spectrum to obtain an extracted signature of the pharmaceutical using the processor.

15. The method of claim 14, wherein the subtracting step comprises solving equation:

$$\vec{X} + \vec{X}_P + \alpha \vec{X}_V,$$

where $\vec{X}$ is the remainder of the acquired spectrum, $\vec{X}_p$ is the extracted signature of the pharmaceutical, $\vec{X}_v$ is the stored calibration spectrum of the closed container, and $\alpha$ is a weighting factor (scalar).

16. The method of claim 15, wherein solving the equation, $\vec{X} = \vec{X}_P + \alpha \vec{X}_V$, for $\vec{X}_p$, the extracted signature of the pharmaceutical, and $\alpha$, the weighting factor comprises using one of an optimization algorithm, a principal component analysis algorithm, a blind source separation algorithm, a Fourier-domain analysis algorithm, or a wavelet-domain analysis algorithm.

17. The method of claim 14, further comprising if the pharmaceutical comprises a known compound, removing a spectrum of the known compound from the remainder of the acquired spectrum to produce a second extracted signature of the pharmaceutical using the processor.

18. The method of claim 17, wherein removing a spectrum of the known compound from the remainder of the acquired spectrum comprises one of an optimization algorithm, a principal component analysis algorithm, a blind source separation algorithm, a Fourier-domain analysis algorithm, or a wavelet-domain analysis algorithm.

19. The method of claim 14, wherein removing a system-response function of the spectrometer from the acquired spectrum using the processor comprises reversing a convolution of the acquired spectrum and the system-response function of the spectrometer.

20. The method of claim 14, wherein removing fluorescence from the acquired spectrum using the processor comprises fitting a baseline spectrum of the fluorescence to the acquired spectrum and removing the baseline spectrum from the acquired spectrum.

21. A method for signature extraction using a software system, comprising:
providing a system, wherein the system comprises distinct software modules embodied on a computer-readable medium, and wherein the distinct software modules comprise a spectrum acquisition module, a system-response correction module, an exposure-time normalization module, a baseline correction module, and an extraction collection module;
obtaining an acquired spectrum of a pharmaceutical from a spectrometer using the spectrum acquisition module, wherein the acquired spectrum is measured through the bottom, side, and or top of a closed container;
storing a calibration spectrum of the closed container using the extraction collection module;
removing a system-response function of the spectrometer from the acquired spectrum using the system-response correction module;
normalizing an intensity of the acquired spectrum to a predetermined scale using the exposure-time normalization module by dividing the intensity by an exposure time of the spectrometer to the pharmaceutical;
removing fluorescence from the acquired spectrum using the baseline correction module; and
subtracting the stored calibration spectrum of the closed container from a remainder of the acquired spectrum to obtain an extracted signature of the pharmaceutical using the extraction collection module.

22. The method of claim 21, wherein the subtracting step comprises solving equation:

$$\vec{X} = \vec{X}_P + \alpha \vec{X}_V,$$

where $\vec{X}$ is the remainder of the acquired spectrum, $\vec{X}_p$ is the extracted signature of the pharmaceutical, $\vec{X}_v$ is the stored calibration spectrum of the closed container, and $\alpha$ is a weighting factor (scalar).

23. The method of claim 22, wherein solving the equation, $\vec{X} = \vec{X}_P + \alpha \vec{X}_V$, for $\vec{X}_p$, the extracted signature of the pharmaceutical, and $\alpha$ the weighting factor comprises using one of an optimization algorithm, a principal component analysis algorithm, a blind source separation algorithm, a Fourier-domain analysis algorithm, or a wavelet-domain analysis algorithm.

24. The method of claim 21, further comprising if the pharmaceutical comprises a known compound, adding a compound subtraction module to the system, removing a spectrum of the known compound from the remainder of the acquired spectrum using the compound subtraction module, and obtaining a second extracted signature of the pharmaceutical from a second remainder of the acquired spectrum using the extraction collection module.

25. The method of claim 24, wherein removing a spectrum of the known compound from the remainder of the acquired spectrum using the compound subtraction module comprises one of an optimization algorithm, a principal component analysis algorithm, a blind source separation algorithm, a Fourier-domain analysis algorithm, or a wavelet-domain analysis algorithm.

26. The method of claim 21, wherein removing a system-response function of the spectrometer from the acquired spectrum using the system-response correction module comprises reversing a convolution of the acquired spectrum and the system-response function of the spectrometer.

27. The method of claim 21, wherein removing the fluorescence from the acquired spectrum using the baseline correction module comprises fitting a baseline spectrum of the fluorescence to the acquired spectrum and removing the baseline spectrum from the acquired spectrum.

28. A computer program product, comprising a non-transient and tangible computer usable medium having a computer readable program code embodied therein, said computer readable program code adapted to be executed to implement a method for signature extraction, comprising:
providing a system, wherein the system comprises distinct software modules embodied on a computer-readable medium, and wherein the distinct software modules comprise a spectrum acquisition module, a system-response correction module, an exposure-time normalization module, a baseline correction module, and an extraction collection module;
obtaining an acquired spectrum of a pharmaceutical from a spectrometer using the spectrum acquisition module, wherein the acquired spectrum is measured through the bottom, side, and or top of a closed container;
storing a calibration spectrum of the closed container using the extraction collection module using the extraction collection module;
removing a system-response function of the spectrometer from the acquired spectrum using the system-response correction module;
normalizing an intensity of the acquired spectrum to a predetermined scale using the exposure-time normalization module by dividing the intensity by an exposure time of the spectrometer to the pharmaceutical;
removing fluorescence from the acquired spectrum using the baseline correction module; and
subtracting the stored calibration spectrum of the closed container from a remainder of the acquired spectrum to obtain an extracted signature of the pharmaceutical using the extraction collection module.

29. The computer program product of claim 28, wherein the subtracting step comprises solving equation:

$$\vec{X} = \vec{X}_P + \alpha \vec{X}_V,$$

where $\vec{X}$ is the remainder of the acquired spectrum, $\vec{X}_p$ is the extracted signature of the pharmaceutical, $\vec{X}_v$, is the calibration spectrum of the closed container, and $\alpha$ is a weighting factor (scalar).

30. The computer program product of claim 28, further comprising if the pharmaceutical comprises a known compound, adding a compound subtraction module to the system, removing a spectrum of the known compound from the remainder of the acquired spectrum using the compound subtraction module, and obtaining a second extracted signature of the pharmaceutical from a second remainder of the acquired spectrum using the extraction collection module.

* * * * *